(12) United States Patent
Lycke

(10) Patent No.: US 11,730,968 B2
(45) Date of Patent: Aug. 22, 2023

(54) WEARABLE MEDICAL DEVICE WITH TEMPERATURE MANAGED ELECTRODES

(71) Applicant: West Affum Holdings Corp., Grand Cayman (KY)

(72) Inventor: Lawrence E. Lycke, Seattle, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 0 days.

(21) Appl. No.: 17/163,576

(22) Filed: Feb. 1, 2021

(65) Prior Publication Data

US 2022/0184406 A1 Jun. 16, 2022

Related U.S. Application Data

(60) Provisional application No. 63/125,308, filed on Dec. 14, 2020.

(51) Int. Cl.
*A61N 1/39* (2006.01)
*A61N 1/28* (2006.01)

(52) U.S. Cl.
CPC .......... *A61N 1/3904* (2017.08); *A61N 1/28* (2013.01); *A61N 1/3968* (2013.01)

(58) Field of Classification Search
CPC ....... A61N 1/3904; A61N 1/3968; A61N 1/28
See application file for complete search history.

(56) References Cited

U.S. PATENT DOCUMENTS

| | | |
|---|---|---|
| 3,724,455 A | 4/1973 | Unger |
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,618,208 A | 4/1997 | Crouse et al. |

(Continued)

FOREIGN PATENT DOCUMENTS

| | | |
|---|---|---|
| EP | 3380189 B1 | 10/2018 |
| WO | 1998039061 A2 | 9/1998 |
| WO | 2012064604 A1 | 5/2012 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Joseph M Dietrich
(74) *Attorney, Agent, or Firm* — Columbia IP Law

(57) ABSTRACT

A wearable cardioverter defibrillator (WCD) system is configured to selectively provide cooling and/or heating to a component of the WCD system. In some embodiments, a Peltier device is used to provide the cooling to wearer of the WCD at or near where the WCDs defibrillation electrodes are positioned proximate or contacting the patient's body.

21 Claims, 12 Drawing Sheets

(56) References Cited

U.S. PATENT DOCUMENTS

| | | |
|---|---|---|
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,067,802 A | 5/2000 | Alonso |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 9,878,171 B2 | 1/2018 | Kaib |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0158634 A1* | 6/2013 | Ron Edoute ........... A61N 1/328 607/101 |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |
| 2020/0101278 A1* | 4/2020 | Freeman ................ A61B 5/259 |
| 2020/0391021 A1* | 12/2020 | Sachs ................... A61N 1/0492 |

OTHER PUBLICATIONS

Lifecor LifeVest System Model WCD 3100 Operator's Manual, 2006, PN 20B0040 Rev Fl, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, p. 2065-2071.

Sahngki Hong, et al. "Wearable thermoelectrics for personalized thermoregulation", Sci. Adv. 5, eaaw0536 (2019).

Reon Pocket とは from Website: https://reonpocket.sony.co.jp/about/.

* cited by examiner

WEARABLE MEDICAL DEVICE WITH TEMPERATURE MANAGED ELECTRODES

CROSS REFERENCE TO RELATED PATENT APPLICATIONS

This patent application claims benefit of U.S. Provisional Patent Application No. 63/125,308 filed on Dec. 14, 2020 entitled "WEARABLE MEDICAL DEVICE WITH TEMPERATURE MANAGED ELECTRODES", the disclosure of which is hereby incorporated by reference for all purposes.

BACKGROUND

Wearable medical devices may include one or more sensors or other components that are placed onto or close to the wearer's body. For example, a person suspected of having an arrhythmia risk may be provided with a wearable medical device called a wearable cardiovert defibrillator (WCD). For example, when a person suffers from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim. A doctor may recommend that this person receive an Implantable Cardioverter Defibrillator ("ICD"). The ICD is surgically implanted in the chest, and continuously monitors the person's electrocardiogram ("ECG"). If certain types of heart arrhythmias are detected, then the ICD delivers an electric shock through the heart.

After being identified as having an increased risk of an SCA, and before receiving an ICD, this person may be given a WCD system. A WCD system typically includes a harness, vest, or other garment for wearing by the patient. The system includes a defibrillator and external electrodes, which are attached on the inside of the harness, vest, or other garment. When a patient properly wears a WCD system, the external electrodes may then make good electrical contact with the patient's skin, and therefore can help monitor the patient's ECG. If a shockable heart arrhythmia is detected, then the defibrillator of the WCD system delivers the appropriate electric shock through the patient's body, and thus through the heart.

BRIEF SUMMARY

In accordance with aspects of this disclosure, a wearable medical device is configured with one or more temperature-controlled components that are proximate to and/or in contact with the wearer's body. For example, in some embodiments, such components can include sensors and/or electrodes, structures of the wearable medical device configured to place such sensors and/or electrodes proximate to and/or in contact with the wearer's body, etc.

The foregoing brief summary is illustrative only and is not intended to be in any way limiting. In addition to the illustrative aspects, embodiments, and features described above, which need not all be present in all embodiments of the inventions disclosed herein, further aspects, embodiments, and features are set forth in the drawings and the following detailed description.

DETAILED DESCRIPTION

Embodiments of wearable medical devices and systems with temperature control systems for support structures and/or sensors in proximity to and/or contacting a wearer's body, temperature control systems for support structures and/or sensors of wearable medical devices, and methods for controlling for the temperature of wearable medical device support structures and/or sensors are, inter alia, disclosed herein.

As mentioned above, some embodiments are directed to wearable medical devices/systems with support structures and/or sensors in proximity to and/or contacting a wearer's body. Wearable medical devices include WCDs, as well as cardiac monitors such as Holter monitors, cardiac assist devices, etc. WCD embodiments are now described.

A WCD system may protect an ambulatory patient by electrically restarting their heart if needed. Such a WCD system may have a number of components. These components can be provided separately as modules that can be interconnected, or can be combined with other components, and so on.

Figure 1:
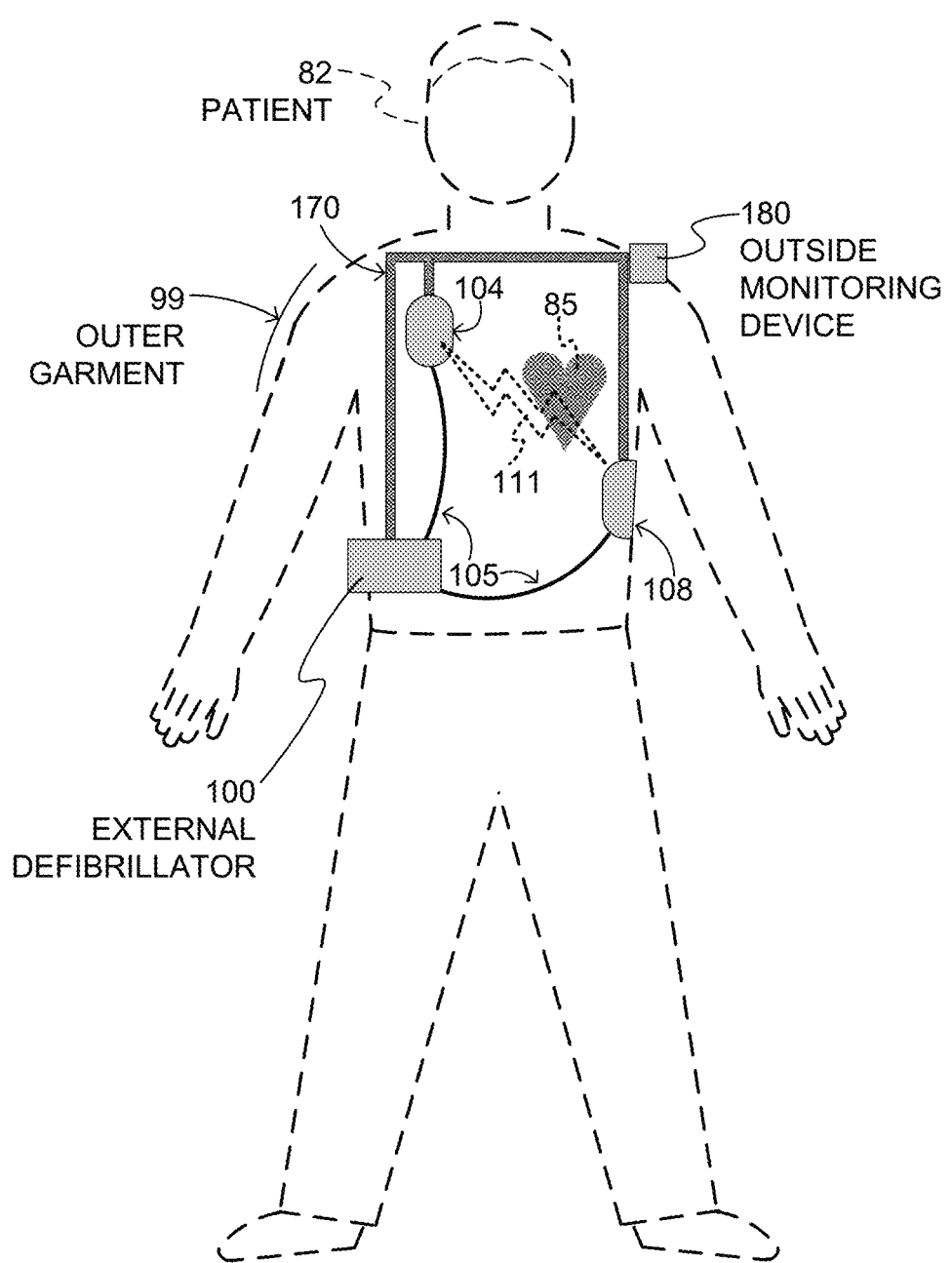
FIG. 1 is a schematic diagram of components of a sample wearable cardioverter defibrillator (WCD) system, according to embodiments.

FIG. 1 depicts a patient 82. Patient 82 may also be referred to as a person and/or wearer since the patient is wearing components of the WCD system. Patient 82 is ambulatory, which means that, while wearing the wearable portion of the WCD system, patient 82 can walk around and is not necessarily bed ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also referred to herein as patient physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
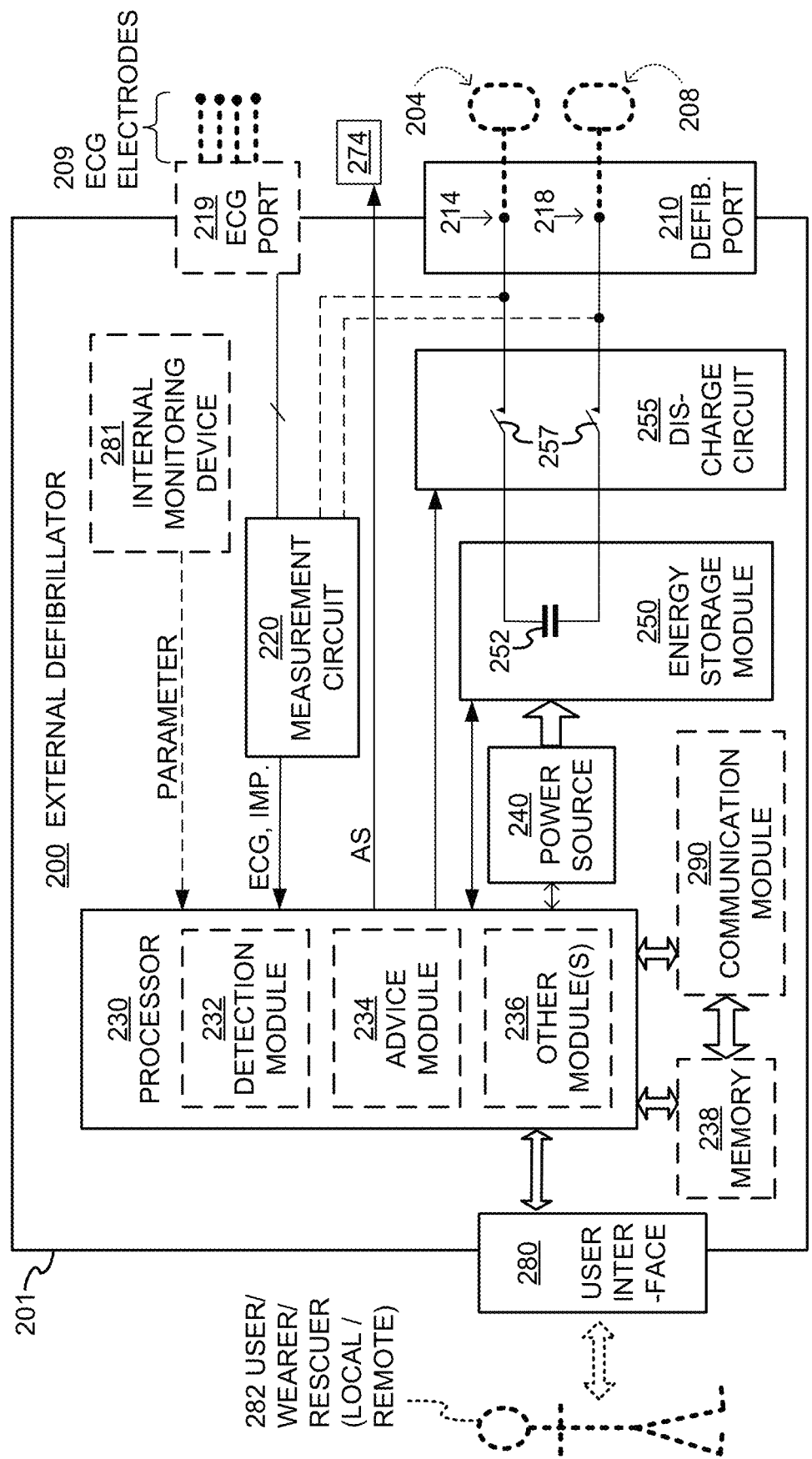
FIG. 2 is a block diagram of sample components of an external defibrillator, such as the one depicted in FIG. 1, according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touch-screens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g. a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In ideal conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018 and since published as US 2019/0030351 A1, and also in U.S. patent application Ser. No. 16/038,007, filed on Jul. 17, 2018 and since published as US 2019/0030352 A1, both by the same applicant and incorporated herein by reference.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. The programs may also include other information such as configuration data, profiles, scheduling etc. that can be acted on by the instructions. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g. on a daily basis, heart rate, respiratory rate, and other vital signs data to a server accessible over the internet, for instance as described in U.S. Published Patent App. Pub. No. 20140043149A1 entitled "MOBILE COMMUNICATION DEVICE & APP FOR WEARABLE DEFIBRILLATOR SYSTEM". This data can be analyzed directly by the patient's physician and can also be analyzed automatically by algorithms designed to detect a developing illness and then notify medical personnel via text, email, phone, etc. Module 290 may also include such interconnected subcomponents as may be deemed necessary by a person skilled in the art, for example an antenna, portions of a processor, supporting electronics, outlet for a telephone or a network cable, etc.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and also by how long discharge circuit 255 is controlled to remain open.

Defibrillator 200 can optionally include other components. In accordance with embodiments of the present disclosure, other such components are included to implement temperature control for support structures and/or sensors (including electrodes) that are in proximity to or in contact with the patient's body. Such temperature control can be advantageous in some embodiments as will described below.

Figure 2A:
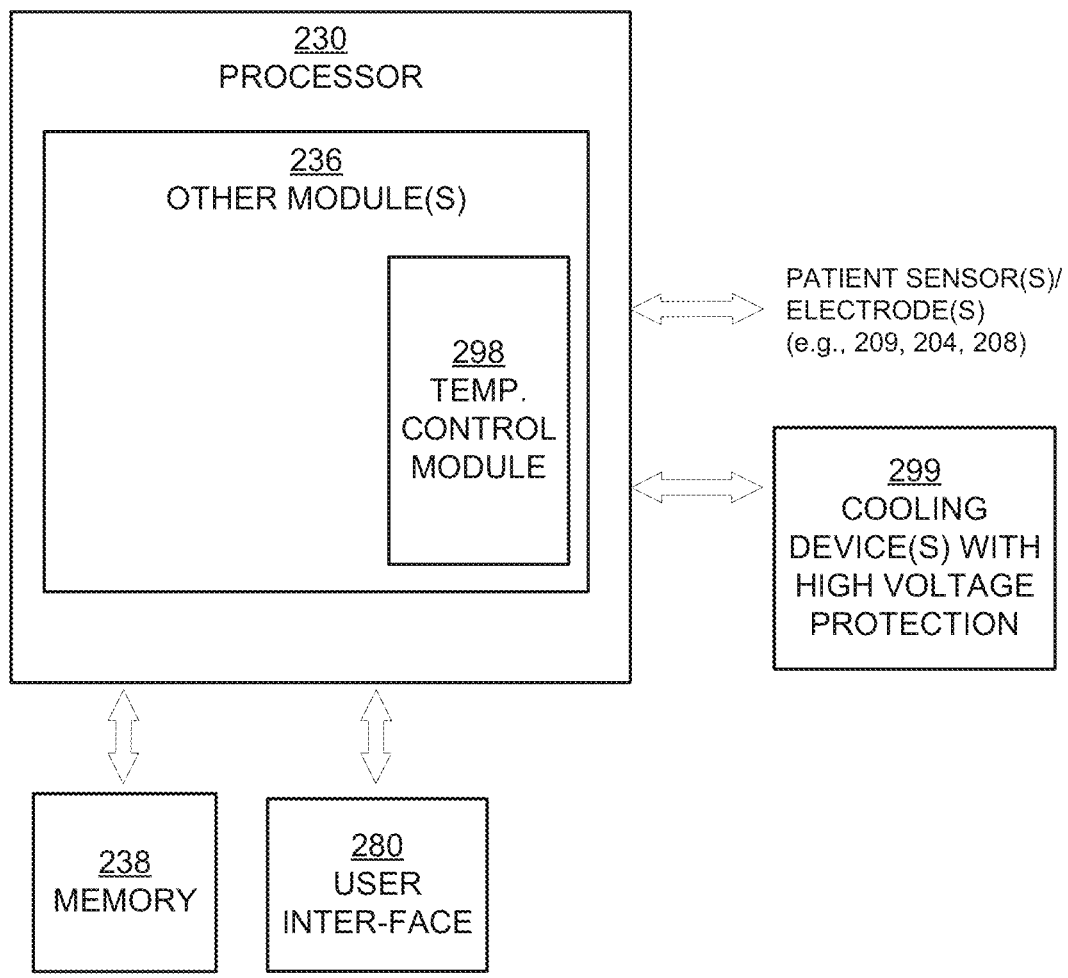
FIG. 2A is a block diagram showing in more detail some of the components depicted in FIG. 2 that are related to temperature control of sensors (including electrodes), according to embodiments.

FIG. 2A is a block diagram showing in more detail some of the components depicted in FIG. 2 that are related to temperature control of WCD components in proximity to and/or in contact with the patient's body such as, for example, sensors and/or electrodes, according to embodiments.

For some wearers of wearable medical devices, there is an increase in temperature at or near these areas of proximity and/or contact, which can cause discomfort for the wearer. This in turn can lead to the wearer taking the wearable device off. When the wearable medical device is a WCD, this is particularly undesirable because the WCD patient can no longer receive potentially life-saving therapy from the WCD. By implementing temperature control according to embodiments of the present disclosure, the wearable medical device can advantageously increase the comfort and thus wear time compliance of the wearer by controlling the temperature at or near the location at which support structures and/or sensors are proximate to and/or contacting the patient's body.

As shown in FIG. 2A, other modules 236 (also in FIG. 2) can include a temperature control module 298. In embodiments, temperature control module 298 can receive user input signals and/or temperature data of the WCD components, and in response provide control signals to one or more cooling device(s) 299 to control the temperature at or near the areas of proximity and/or contact. Cooling device(s) 299 may be in proximity to or coupled to the WCD components. For example, in some embodiments, cooling devices may be coupled to defibrillation electrodes 204 and 208 (FIG. 2). In other embodiments, cooling device(s) 299 may be coupled to other combinations of WCD components such as, for example, ECG electrodes, and/or portions of support structure 170 (FIG. 1) that tend to trap heat against the patient's skin. Although WCD embodiments have been described, temperature control module 298 and cooling device(s) 299 may be used in other types of wearable medical devices such as, for example, wearable cardiac monitors (e.g., Holter monitors), ventricular assist devices/systems, wearable peritoneal dialysis devices, etc. Embodiments of cooling device(s) 299 may be implemented as described below in conjunction with FIGS. 5-12.

Figure 3:
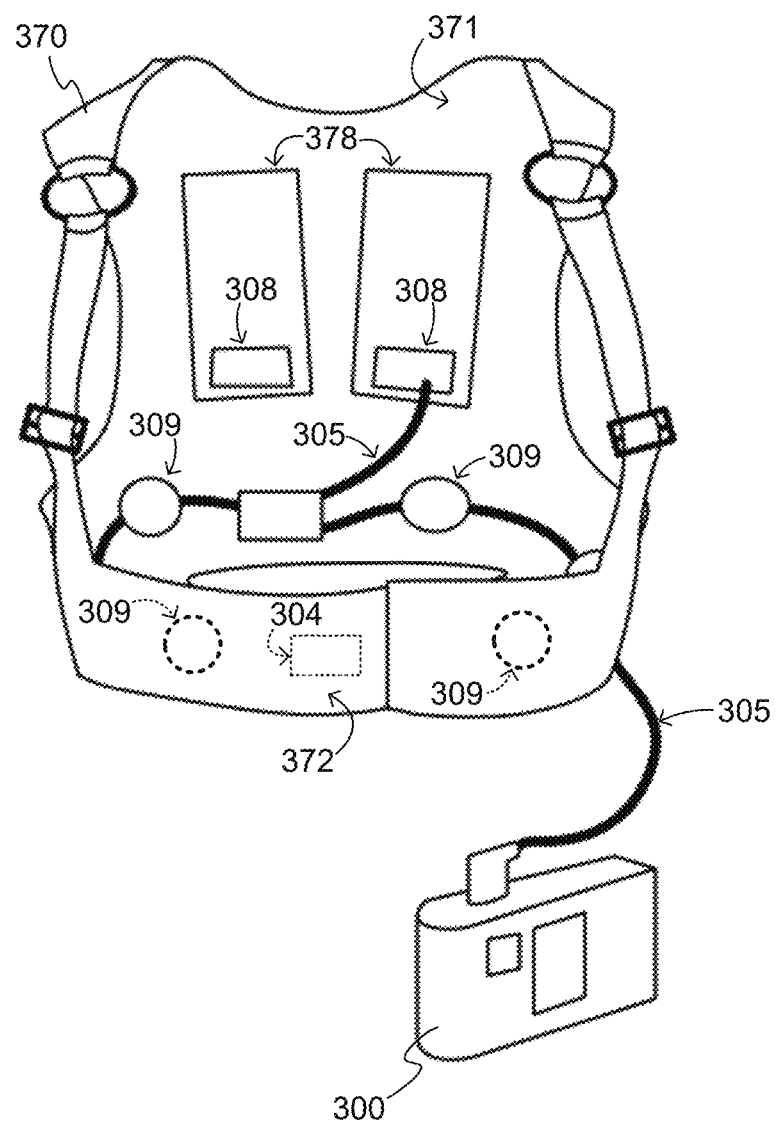
FIG. 3 is a diagram illustrating components of a WCD system with illustrative placement of some components on a support structure, according to embodiments.

FIG. 3 is a diagram of sample embodiments of components of an WCD system. A support structure 370 includes a vest-like wearable garment. Support structure 370 has a back side 371, and a front side 372 that closes in front of the chest of the patient.

The WCD system of FIG. 3 also includes an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the ambulatory patient so as to maintain electrodes 304, 308, 309 on a body of the patient. In some embodiments, back defibrillation electrodes 308 are maintained in pockets 378. In some embodiments, the inside of pockets 378 can be made with loose netting or permeable conductive fabric, so that defibrillation electrodes 308 can contact the back of the patient, especially with the help of the conductive fluid that has been deployed. In addition, sensing electrodes 309 are maintained in positions that surround the patient's torso, for sensing ECG signals and/or the impedance of the patient.

In accordance with embodiments of the present disclosure, sensors or other components that are in close proximity and/or contact the patient's skin (for example defibrillation electrodes 304 and/or 308) can be implemented with temperature control as described below in conjunction with FIGS. 5-12. In some embodiments, the temperature control is implemented using Peltier cooling devices. In some embodiments, the temperature control is implemented by cooling one or more portions of support structure 370 such as, for example, pockets 378. In some embodiments, pockets 378 include an electrically conductive mesh to facilitate electrical contact of defibrillation electrodes 309 with the patient's skin, with the conductive mesh also being part of the Peltier cooling device(s). In some embodiments, cooling device(s) are coupled to cool the mesh in addition to or instead of cooling the defibrillation electrode(s).

ECG signals in a WCD system may include too much electrical noise to be useful. To ameliorate the problem, multiple ECG sensing electrodes 309 are provided, for presenting many options to processor 230. These options are different vectors for sensing the ECG signal, as described now in more detail.

Figure 4:
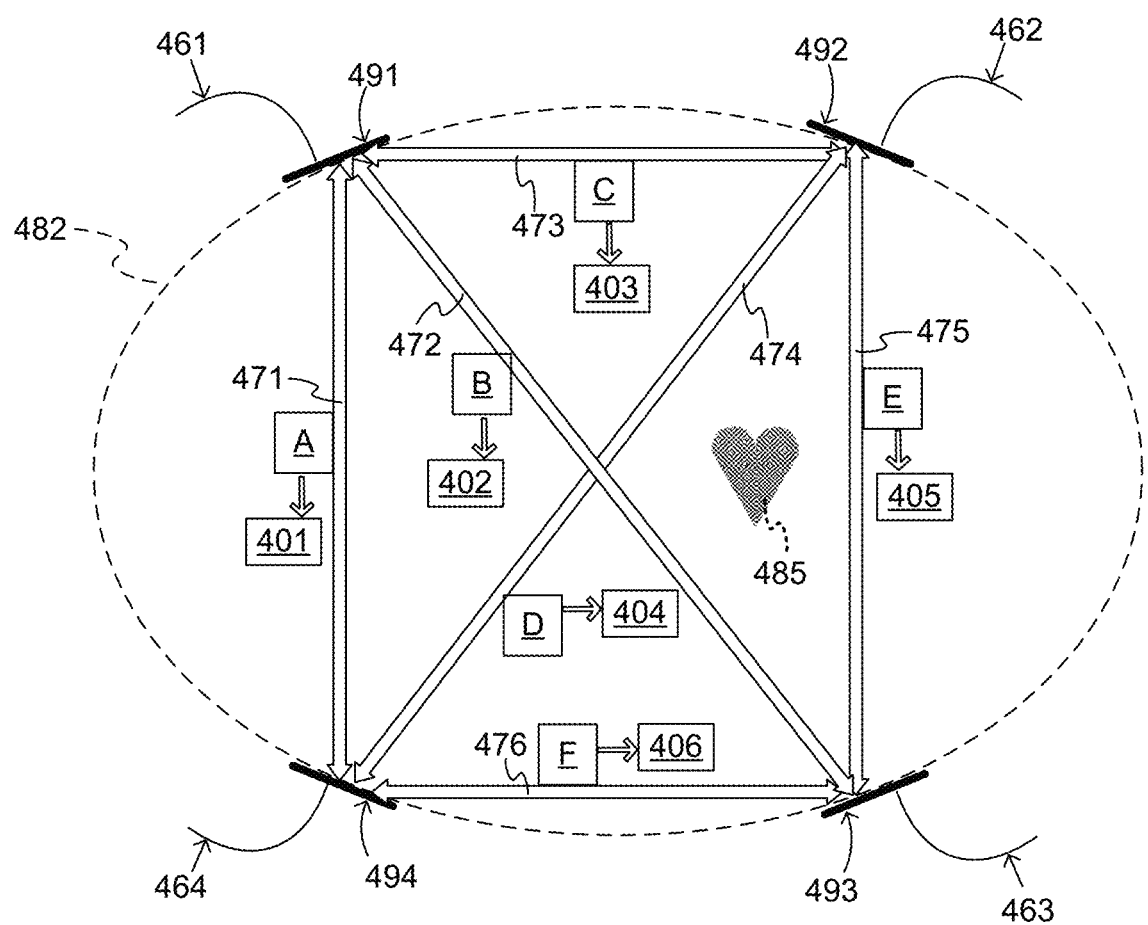
FIG. 4 is a conceptual diagram illustrating how multiple electrodes of a WCD system may be used for sensing ECG signals along different vectors according to embodiments.

FIG. 4 is a conceptual diagram for illustrating how multiple electrodes of a WCD system may be used for sensing ECG signals along different vectors according to embodiments. A section of a patient 482 having a heart 485 is shown. In FIG. 4, patient 482 is viewed from the top, patient 482 is facing downwards, and the plane of FIG. 4 intersects patient 482 at the torso of the patient.

Four ECG sensing electrodes 491, 492, 493, 494 are maintained on the torso of patient 482, and have respective wire leads 461, 462, 463, 464. It will be recognized that electrodes 491, 492, 493, 494 surround the torso, similarly with sensing electrodes 309 in the example of FIG. 3.

Any pair of these four ECG sensing electrodes 491, 492, 493, 494 defines a vector, along which an ECG signal may be sensed and/or measured. As such, electrodes 491, 492, 493, 494 define six vectors 471, 472, 473, 474, 475, 476. FIG. 4 thus illustrates a multi-vector embodiment.

These vectors 471, 472, 473, 474, 475, 476 define channels A, B, C, D, E, F respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

In FIG. 4 it will be understood that electrodes 491, 492, 493, 494 are drawn as being on the same plane for simplicity and as is preferred, while that is not necessarily the case. Accordingly, vectors 471, 472, 473, 474, 475, 476 are not necessarily on the same plane, either. Further, some embodiments average value of the voltages of all four electrodes electronically and then determine the voltage of each electrode relative to the average value. Conceptually this average value is the signal at some point in space in between the 4 electrodes. It continuously changes its virtual position based on the voltages of the 4 electrodes. In some embodiments, this virtual point is referred to herein as the M Central Terminal (MCT). Relative to the MCT, there are four resulting vectors: E1C=E1−CM, E2C=E2−CM, E3C=E3−CM and E4C=E4−CM, where CM is the average voltage value. In embodiments, the vectors are formed in software by selecting a pair of these signals and subtracting one from the other. So for example, E1C−E2C=(E1−CM)−(E2−CM) =E1−E2+(CM−CM)=E1−E2=E12. Although six vectors are described in FIG. 4, in other embodiments a different number of vectors may be vectors may be used depending on the number of ECG electrodes used in the system and the desired number of vectors (up to the number of vectors than can be derived from the number of electrodes).

In embodiments, in order to make the shock/no-shock determination as correctly as possible, a WCD may assess which of ECG signals 401, 402, 403, 404, 405, 406 is best for rhythm analysis and interpretation. For example, ECG signals that have the most noise may be ignored, discarded, not considered, while leaving the remaining ECG signals as candidates for making the shock/no shock determination.

In other embodiments, the vectors may be aggregated to make a shock/no shock decision, and/or to determine the patient's heart rate and/or QRS widths. For example, in some embodiments the aggregation can be implemented as disclosed in U.S. Pat. No. 9,757,581 issued Sep. 12, 2017 entitled "WEARABLE CARDIOVERTER DEFIBRILLATOR COMPONENTS MAKING AGGREGATE SHOCK/NO SHOCK DETERMINATION FROM TWO OR MORE ECG SIGNALS", which is incorporated herein by reference.

Figure 5:
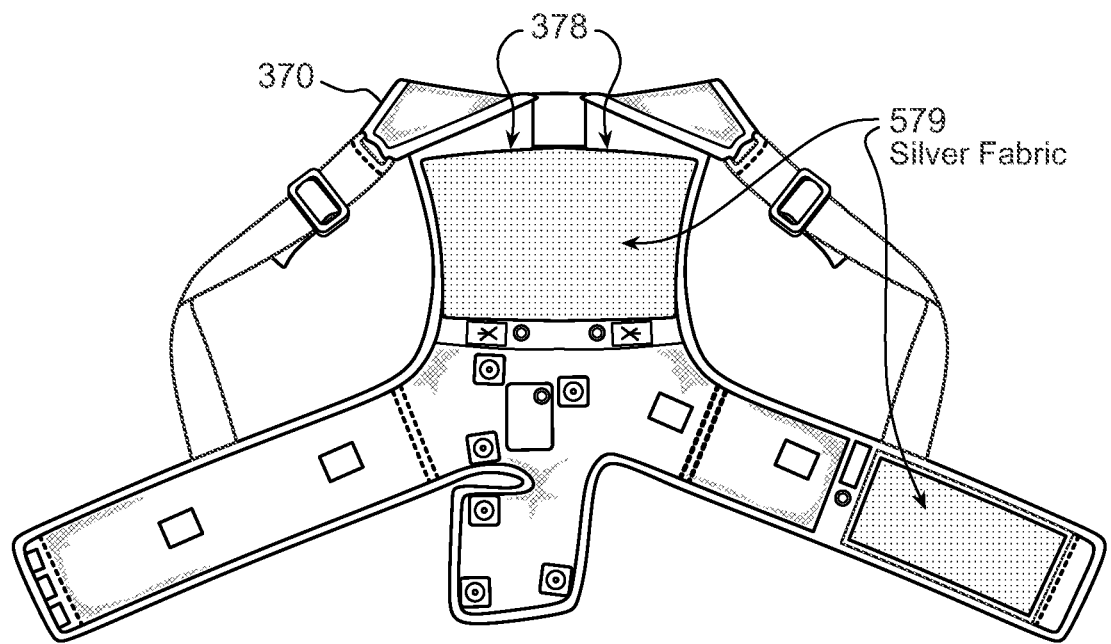
FIG. 5 is a diagram illustrating an example support structure with gel permeable conductive fabric for defibrillation electrodes, according to embodiments.

FIG. 5 is a diagram illustrating an example support structure with gel permeable conductive fabric for defibrillation electrodes, according to embodiments. In embodiments, pockets 378 (see also FIG. 3) of support structure 370 are implemented with gel permeable conductive fabric 579. In some embodiments, the gel permeable conductive fabric 579 may include a silver- or silver-plated thread on the portions of pockets 378 that contact the patient's skin when support structure 370 is worn by the patient. Silver is a material with relatively high electrical and thermal conductivity and, as will be described below, can be advantageously used with Peltier devices. In other embodiments, different materials with relativity high electrical and thermal conductivity may be used.

Figure 6:
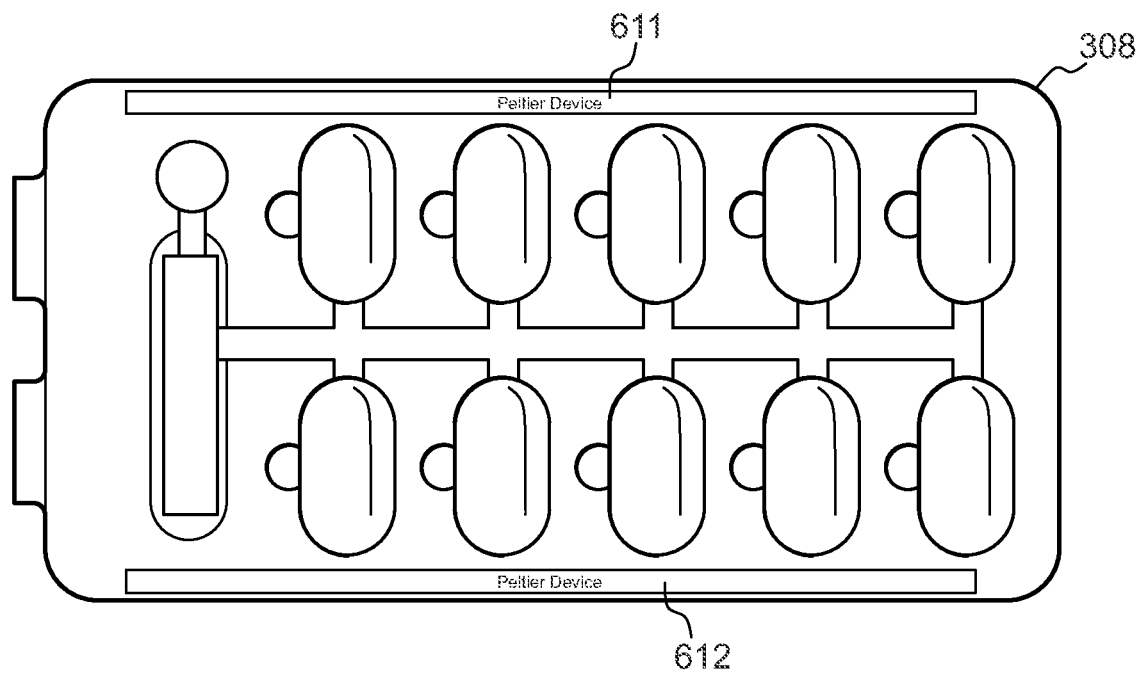
FIG. 6 is a diagram illustrating an example defibrillation electrode with gel packs and Peltier cooling devices, according to embodiments.

FIG. 6 is a diagram illustrating an example defibrillation electrode with gel packs and Peltier cooling devices, according to embodiments. FIG. 6 schematically illustrates a top view of an example defibrillation electrode 308 with two Peltier devices 611 arranged on opposing sides of the assembly. Peltier devices can be used to transfer heat (see for example, U.S. Pat. No. 6,067,802 entitled "PELTIER EFFECT HEAT PUMP"). The oval shapes represent reservoirs for holding gel, the circles adjacent to the reservoirs represent openings for the gel to disperse onto the patient's skin when the reservoirs are pressurized by a gas provided by a gas generator through channels connected to the reservoirs. In other embodiments, additional Peltier devices or "patches" can be added to the assembly at various locations on the defibrillation electrode. In other embodiments a single Peltier device can be added to the electrode assembly, with the single device being shaped to weave around the gel pack reservoirs, etc.

In some embodiments, Peltier devices 611 have portions or structures that are attached to or held in contact with the conductive portion(s) of defibrillation electrode 308 (i.e., on the bottom side of the depicted defibrillation electrode) that typically contact the patient's skin and other portions at the top side of the defibrillation electrode assembly that serve as heat sinks or dissipators. In some embodiments, these conductive portion(s) of the defibrillation electrode are positioned to be into electrical contact with the patient's skin via gel permeable conductive fabric (e.g., such as fabric 579 described above in conjunction with FIG. 5) while the patient is wearing support structure 370 (FIG. 3). Peltier devices 611 operate to move heat from the conductive defibrillation electrode portion(s) to the "top" of the electrode assembly, thereby cooling the portion of the patient's skin proximate to the defibrillation electrode 308.

Figure 7:
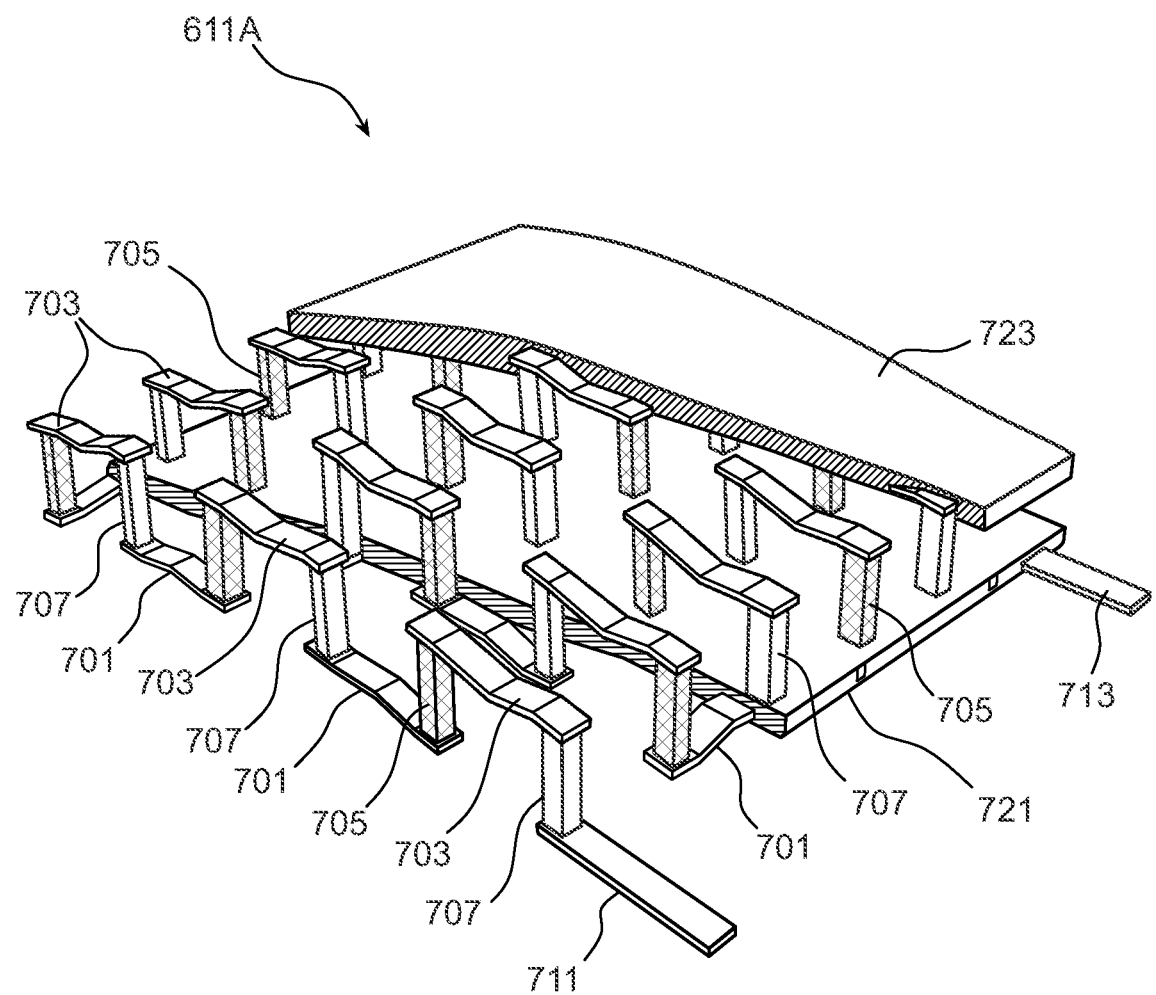
FIG. 7 is a diagram illustrating an example Peltier cooling device, according to embodiments.

FIG. 7 is a partial cut-away diagram illustrating an example Peltier device 611A, according to embodiments. In some embodiments, Peltier device 611A is similar to thermoelectric devices (TEDs) as disclosed in "Wearable Thermoelectrics for Personalized Thermoregulation" Hong et al., Sci. Adv. 2019; 5: eaaw0536 17 May 2019, but improved to enable a Peltier device to be used in defibrillation electrode assemblies. The Hong et al. paper is hereby incorporated by reference in its entirety for all purposes. Currently available Peltier devices are not believed to account for the unique challenges of WCD applications. For example, one such improvement enables Peltier device 611A to withstand the high voltages experienced when a defibrillation shock is delivered to the patient. Another improvement enables Peltier device 611A to be used for extended periods of time (e.g., 22 hours per day).

As shown in FIG. 7, Peltier device 611A as conductor segments 701 located in a "bottom layer", and conductor segments 703 located at a "top layer". Bottom layer segments 701 are serially connected to top layer segments 703 in alternating fashion via thermoelectric (TE) pillars 705 and 707. In some embodiments, TE pillars 705 are made of a low thermal conductivity material of one polarity (e.g., n-type), while TE pillars 707 are made of a low thermal conductivity material of opposite polarity (e.g., p-type if TE pillars are n-type). In other embodiments, the TE pillars may be implemented in other ways such as, for example, with layered materials forming p/n junctions. The serially connected conductor segments are coupled to a power source (not shown) via conductor segments 711 and 713, which depending on the polarity of the voltage causes Peltier device 611A to transfer heat to/or from bottom layer conductive segments 701 to top layer conductive segments 703. In embodiments, conductor segments 711 and 713 are connected to a high voltage protection circuit (not shown), which in turn is connected to the power source and circuitry for controlling the powering of Peltier device 611A. For example, the high voltage protection circuit for protecting ECG sensor circuitry described in US Publ. Pat. App. No. 20190159696 filed Nov. 20, 2018 and entitled "WEARABLE CARDIOVERTER DEFIBRILLATOR WITH IMPROVED ECG ELECTRODES" can be used to protect the circuitry of controlling and powering Peltier device 611A. US Publ. Pat. App. No. 20190159696 is hereby incorporated by reference in its entirety for all purposes. The control circuitry can include a thermocouple circuitry to sense the temperature difference between the top and bottom conductive segments 703 and 701. The control circuitry can use the sensed temperature to control the cooling/heating effect of Peltier device 611A (e.g., by using pulse width modulation in powering Peltier device 611A.

Peltier device 611A also includes a bottom thermally conductive dielectric layer 721 and a top thermally conductive dielectric layer 723. As shown by the "cut-way" portion of layers 721 and 723 in FIG. 7, conductive segments 701 are embedded in thermally conductive dielectric layer 721, and conductive segments 703 are embedded in thermally conductive dielectric layer 723. In some embodiments, layers 721 and 723 are made of a stretchable rubber-type material embedded with Aluminum nitride power to increase thermally conductivity of the layers. In some embodiments, layers 721 and 723 are formed with an air gap between the layers to enable relatively high flexibility, while in other embodiments a flexible non-conductive fill material is used to provide a relatively high structural integrity to Peltier device 611A.

Although Peltier device 611A has a rectangular configuration in the example of FIG. 7, in other embodiments, conductive segments 701 and 702 can be serially connected as previously described into different shapes suited for the application. For example, some embodiments can be arranged as straight strips that fit along the periphery of a defibrillation electrode, or a or complex arrangement where the strip weaves between structures on the defibrillation electrode. In some embodiments, the TE pillars are approximately 1 mm×1 mm×5 mm and spaced apart by approximately 3 mm; while the conductive segments are approximately 5 mm long and 1 mm wide.

In some other embodiments, Peltier device 611A above is modified so that the electrode strips and the stretchable sheets are replaced with materials that are less stretchable for therapy electrodes that are relatively stiff. With the less strict stretchability requirement, the top and bottom sheets may be made of less expensive and/or more thermally conductive materials. In some embodiments, Peltier device 611A further modified to be waterproof (e.g., hermetically sealing the stretchable sheets so that all of the flexible electrode strips and TE pillars are protected from moisture). The waterproof Peltier device can be integrated into the garment or support structure (which can be washable) rather than the defibrillation electrode assembly. For example, the waterproof Peltier device can be integrated around the periphery of pockets 378 (FIG. 5) used to receive/position the therapy electrode assembly in the garment or support structure.

Peltier devices can also be configured to capture energy from a temperature differential. When the power source is switch out of the Peltier device, a temperature difference between the top and bottom layer will cause a voltage to appear at the ends of the now open-circuit (e.g., conductor segments 711 and 713 in FIG. 7). This is sometimes referred to as the Seebeck Effect. In some embodiments instead of using the power source to transfer heat, Peltier device 611A can be configured to switch out the power source and switch in a circuit to capture energy. For example, the voltage at conductor segments 711 and 713 can be used to drive a charge pump to store energy for use by the Peltier device during times the patient does not want the cooling functionality.

Referring back to FIG. 2A, in some embodiments, when the patient is experiencing heat under defibrillation electrode, the patient can provide a user input to temperature control module 298 via user interface 280 to activate cooling device(s) 299, which can be implemented as described above for Peltier device 611A (FIG. 7). In some embodiments, temperature control module 298 is configured to operate cooling device(s) 299 for a specified period of time to provide cooling. In other embodiments, cooling device(s) 299 is operated in a cyclic or periodic manner, cooling for a period of time and turning off for a period of time. In other embodiments, cooling device(s) 299 and/or its associated patient sensor(s)/electrode(s) may include a temperature sensor, which temperature control module 298 may use to control cooling device(s) 299 to maintain the temperature with a specified range. The temperature can be controlled to a temperature relative to normal body temperature (as opposed to cooler temperatures associated with air conditioning). For example, this comfort level may be around 36 Celsius under the therapy pads (slightly below normal body temperature), which may serve to reduce power consumption. In some embodiments, cooling device(s) 299 may be configured with its own power source or alternatively to receive power from an external source. For example, if the patient is going on a long car drive (in which the seat may strongly press the defibrillation electrodes into contact with the patient's skin and increasing the temperature under the defibrillation electrodes), cooling device(s) 299 may include a power input from a USB, automobile 12v outlet (accessary outlet), or an inductive charging unit (e.g., Qi) more strongly. The external power can allow the cooling to continue with less concern about power consumption.

Figure 8:
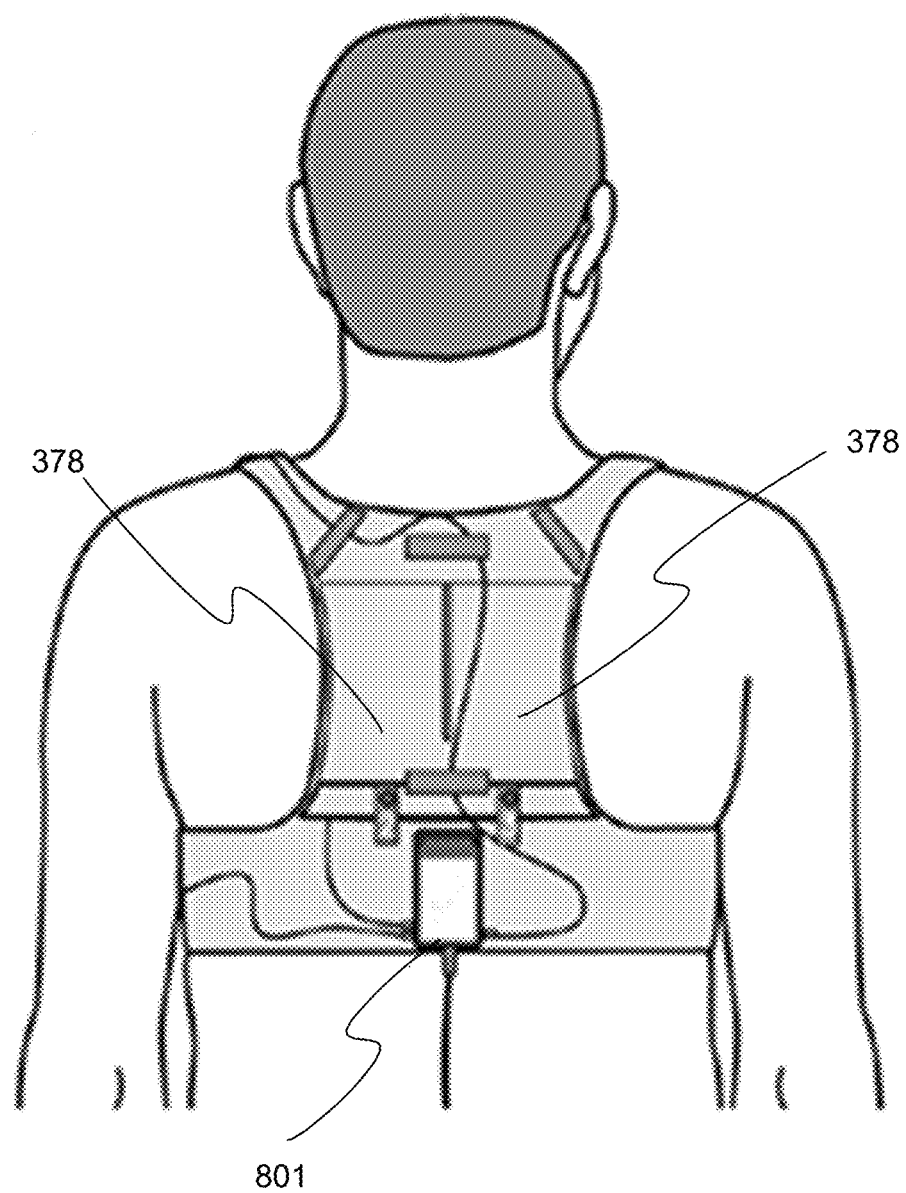
FIG. 8 is a diagram illustrating an example Peltier cooling device with illustrative placement on a WCD support structure, according to embodiments.

FIG. 8 is a diagram illustrating an example Peltier cooling device with illustrative placement on a WCD support structure, according to embodiments. In embodiments, a module 801 is attached to the support structure at a location between the patient's shoulder blades as shown in FIG. 8. In some embodiments, module 801 includes power source and control circuitry, similar to that described above in conjunction with FIG. 7.

In other embodiments, in addition to a Peltier device, module 801 includes electronics for receiving and processing sensor signals (e.g., ECG signals from ECG sensors such as shown in FIG. 1) and transmitting the processed ECG signals to another module (e.g., an external defibrillator monitor). For example, the electronics module may filter and perform analog-to-digital conversion of received ECG signals before transmitting them to the external defibrillator. In some embodiments, the electronics also include a motion sensor such as an accelerometer. The Peltier device can be integrated into module 801 with conductive surfaces extending between and/or around pockets 378 for defibrillation electrodes that do not have Peltier devices. In some embodiments, module 801 shaped, and adapted to fit into a pocket located between pockets 378, rather than below pockets 378 as shown in FIG. 8.

In other embodiments, module 801 includes a Peltier device similar to the Reon Pocket available from Sony, but modified with high voltage circuitry as previously described. The Reon Pocket is described at https://reonpocket.sony.co.jp/. In these embodiments, an outer garment worn by the patient over the WCD support structure can include a vent or mesh to allow the Peltier device to blow the heated air away from the patient.

In some alternative embodiments, the Peltier device (not shown in FIG. 8) is separate from module 801, which is configured with the electronics for receiving and processing sensor signals described above. In these embodiments, the Peltier device is removeable and not dependent on the wearable medical device (e.g., temperature control module 298) for control, but does include high voltage protection circuitry and a power source and control circuitry. In some embodiments, the Peltier device as a wireless communication module through which the patient may wirelessly control the Peltier device via a separate interface, such as an app loaded onto the patient's smart device. In some embodiments, the therapy electrodes may be shaped with (e.g., concave sides) to provide more room for the Peltier device between pockets 378. In some embodiments, the Peltier device is thermally connected to thermally conductive mesh of pockets 378.

In other embodiments, the Peltier device may have a fan used to dissipate heat from the "hot" side or heat sink of the Peltier device. In a further enhancement, the fan can be modified to divert a portion of the moving air before the air reaches the heat sink using tubing. The tubing directs this air to the defibrillation electrode assembly. The defibrillation electrode assembly is configured to receive this and direct it through the channels of the gel pack used for dispensing the gel onto the patient's skin. In embodiments, the tubing can have a one-way flap type valve to allow air to flow into the defibrillation electrode assembly and prevent dispensed gel from flowing out from the assembly to the Peltier device. This air flow can help dissipate heat from under the therapy pad assembly and/or facilitate moisture evaporation. This airflow can be relatively small and intermittent to achieve the cooling effect and/or moisture control, while still allowing portions of the therapy electrode to stay in contact with the patient skin. The air flow can be controlled to stop when the WCD is preparing to deliver a shock so that the defibrillation electrode maintains contact with the patient's skin. Instead of stopping the air flow, in some embodiments the air flow is diverted to a bladder disposed on the defibrillation electrode assembly such that when the bladder is inflated it exerts a force on the defibrillation electrode to maintain or improve contact with the patient's skin. In some embodiments, the tubing is thermally coupled to the "cold" side of the Peltier device to be cooled before entering the electrode assembly channels to enhance the cooling effect.

The various embodiments of the devices and/or systems disclosed in this document perform functions, processes and/or methods as described above. These functions, processes and/or methods may be implemented by one or more devices that include logic circuitry. Such a device can be alternately called a computer, and so on. It may be a standalone device or computer, such as a general-purpose computer, or part of a device that has one or more additional functions. In some embodiments, the computer is a specialized computer adapted to and optimally configured for a specific purpose such as for example, providing therapy shocks in emergency situations. The logic circuitry may include a processor and non-transitory computer-readable storage media, such as memories, of the type described in this document. Often, for the sake of convenience, it is preferred to implement and describe a program as various interconnected distinct software modules or features. These, along with data are individually and also collectively referred to herein as software. In some instances, software is combined with hardware, in a mix called firmware.

Various embodiments of methods and algorithms are described below. These methods and algorithms are not necessarily inherently associated with any particular logic device or other apparatus. Rather, they can be advantageously implemented by programs for use by a computing machine, such as a general-purpose computer, a special purpose computer, a microprocessor, a microcontroller, a processor and/or a combination of these devices such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts describe methods in terms of boxes, they also concurrently describe programs.

Figure 9:
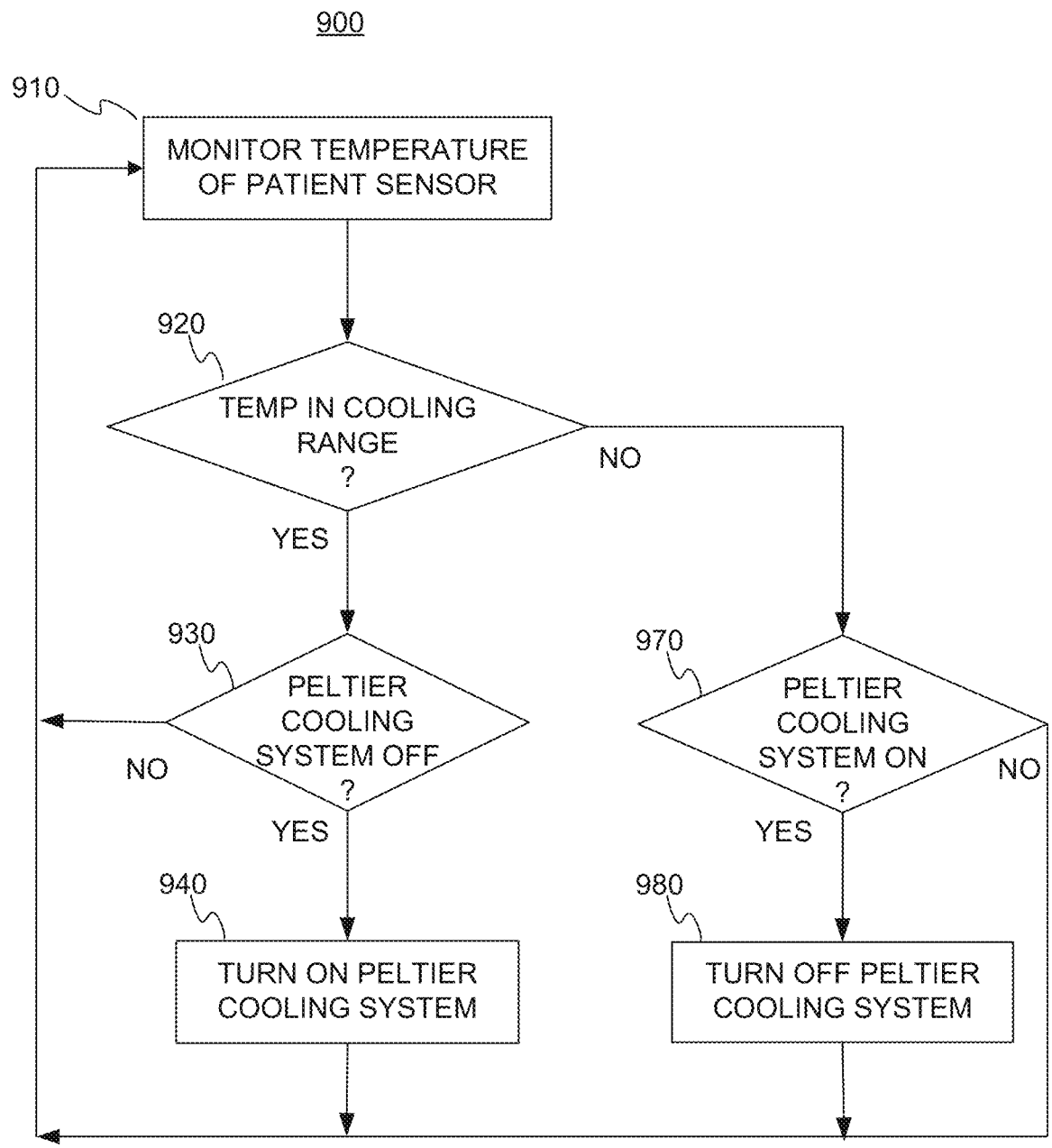
FIG. 9 is a flow diagram illustrating sample methods for use in a wearable medical device system to cool a portion of a patient and/or one or more patient sensors, according to embodiments.

FIG. 9 is a flow diagram illustrating embodiments of a method 900 for use in wearable medical device systems (such as described above) to cool a portion of a patient and/or one or more patient sensors, according to embodiments. The process implemented by method 900 may be performed by a temperature control module such as temperature control module 298 described above in conjunction with FIG. 2A in some embodiments.

In a block 910, a temperature of a component of the wearable medical device is monitored. For example, in a WCD embodiment, a temperature control module such as temperature control module 298 (FIG. 2A) monitors the temperature of one or more of a patient physiological parameter sensor (e.g., ECG sensor), a defibrillation electrode, a portion of the support structure (e.g., conductive fabric 579 of FIG. 5), the cooling device "output" (e.g., cooling device 299 of FIG. 2A), etc. Although the temperature of any of the foregoing components may be monitored in block 910, to simplify FIG. 9, block 910 uses the term "patient sensor" to refer to all of these components.

In a block 920 the monitored temperature is analyzed to determine if it is in a predetermined range (e.g., a cooling range). In some embodiments, this range can be set or adjusted by the patient. For example, in a WCD embodiment, the temperature control module mentioned in block 910 may perform this analysis. This temperature range allows for the cooling system to be turned on at certain temperature, and turned off after the cooling reaches a certain lower temperature. If in block 920 the temperature is within the cooling range method 900 proceeds to a block 930.

In block 930, the cooling system (e.g. a cooling device such as Peltier device 611A of FIG. 7) is checked to see if it is turned on. If the cooling device is turned off, method 900 returns to block 910. However, if the cooling device is turned on, the process proceeds to a block 940 in which the cooling system is turned off and then loops back to block 910.

However, if in block 920 the temperature is not in the cooling range, method 900 proceeds to a block 970 to determine if the cooling system is turned on. If the cooling system is not turned on, method 900 returns to block 910 to continue monitoring the temperature. However, if the cooling device is turned on, method 900 proceeds to a block 980 in which the cooling system is turned off. Method 900 then returns to block 910. Note, in other embodiments, cooling systems other than Peltier systems may be used.

Figure 10:
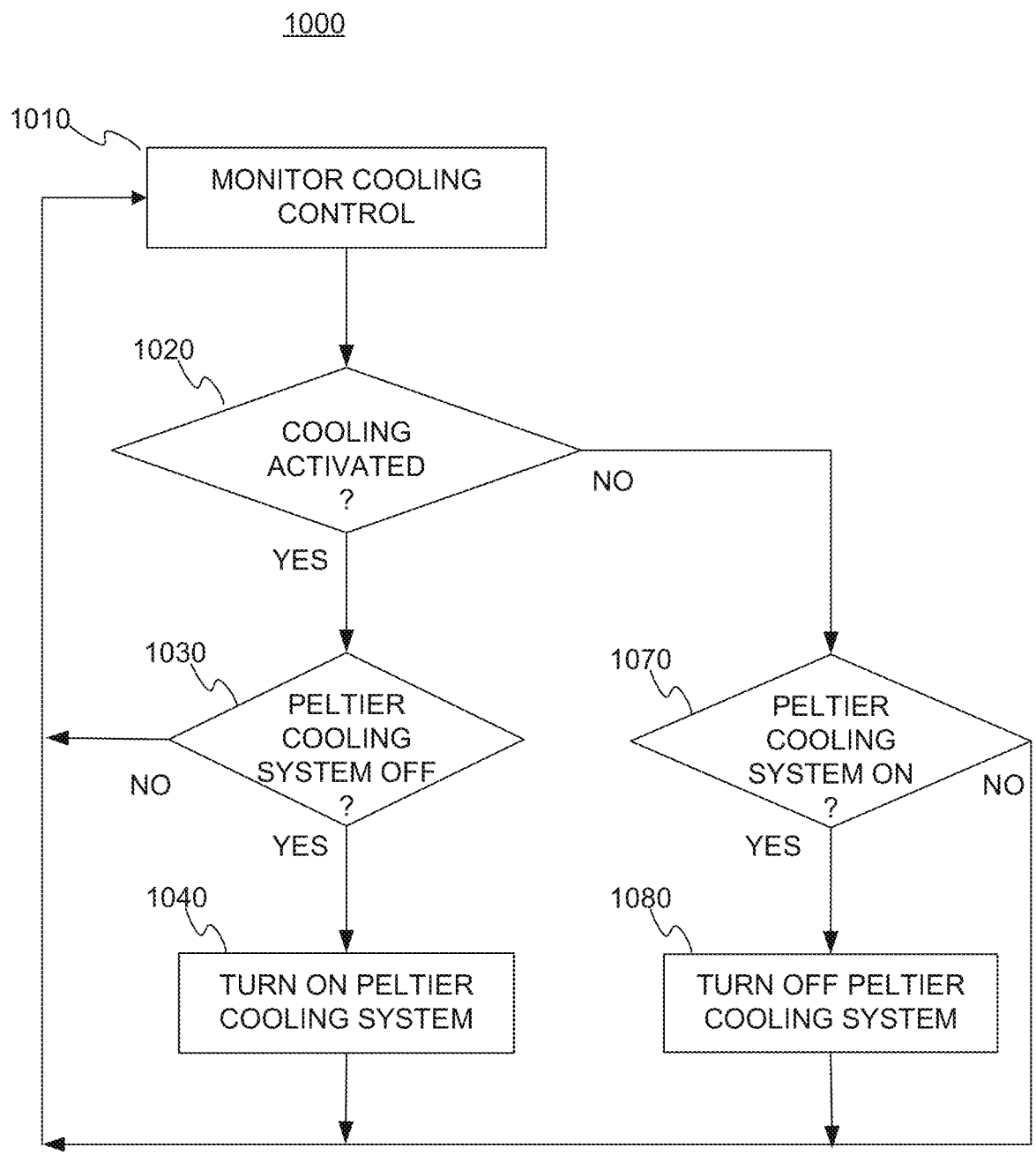
FIG. 10 is a flow diagram illustrating sample methods for use in a wearable medical device system to cool a portion of a patient and/or one or more patient sensors, according to embodiments.

FIG. 10 is a flow diagram illustrating embodiments of a method 1000 for use in wearable medical device systems (such as described above) to cool a portion of a patient and/or one or more patient sensors, according to embodiments. The process implemented by method 1000 may be performed by a temperature control module such as temperature control module 298 described above in conjunction with FIG. 2A in some embodiments. Method 1000 can be used to enable wearer control of the cooling system, rather than using a temperature monitoring approach, so that the wearer can activate the cooling only when he or she desires.

In a block 1010, a cooling control is monitored for activation by the wearer of the wearable medical device. In some embodiments, the cooling control is a user interface that the wearer can operate to turn on or turn off the cooling system.

Method 1000 then proceeds to a block 1020 in which it is determined or detected whether the wearer turned on the cooling system. If in block 1020 it is determined or detected that the wearer did activate the cooling system, method 1000 proceeds to a block 1030.

In block 1030, the cooling system (e.g. a cooling device such as Peltier device 611A of FIG. 7) is checked to see if it is turned off. If the cooling device is turned on, method 1000 returns to block 1010. However, if the cooling device is turned off, method 1000 proceeds to a block 1040 in which the cooling system is turned on and loops back to block 1010. In some embodiments the cooling device stays turned on until the wearer turns it off, while in other embodiments, turning on the cooling device causes it to operate within a temperature range such as described above in conjunction with FIG. 9.

However, if in block 1020 the wearer did not activate the cooling system, method 1000 proceeds to a block 1070 to determine if the cooling system is turned on. If the cooling system is not turned on, method 1000 returns to block 1010 to continue monitoring the temperature. However, if the cooling device is turned on, method 1000 proceeds to a block 1080 in which the cooling system is turned off. Method 1000 then returns to block 1010. Note, in other embodiments, cooling systems other than Peltier systems may be used.

Figure 11:
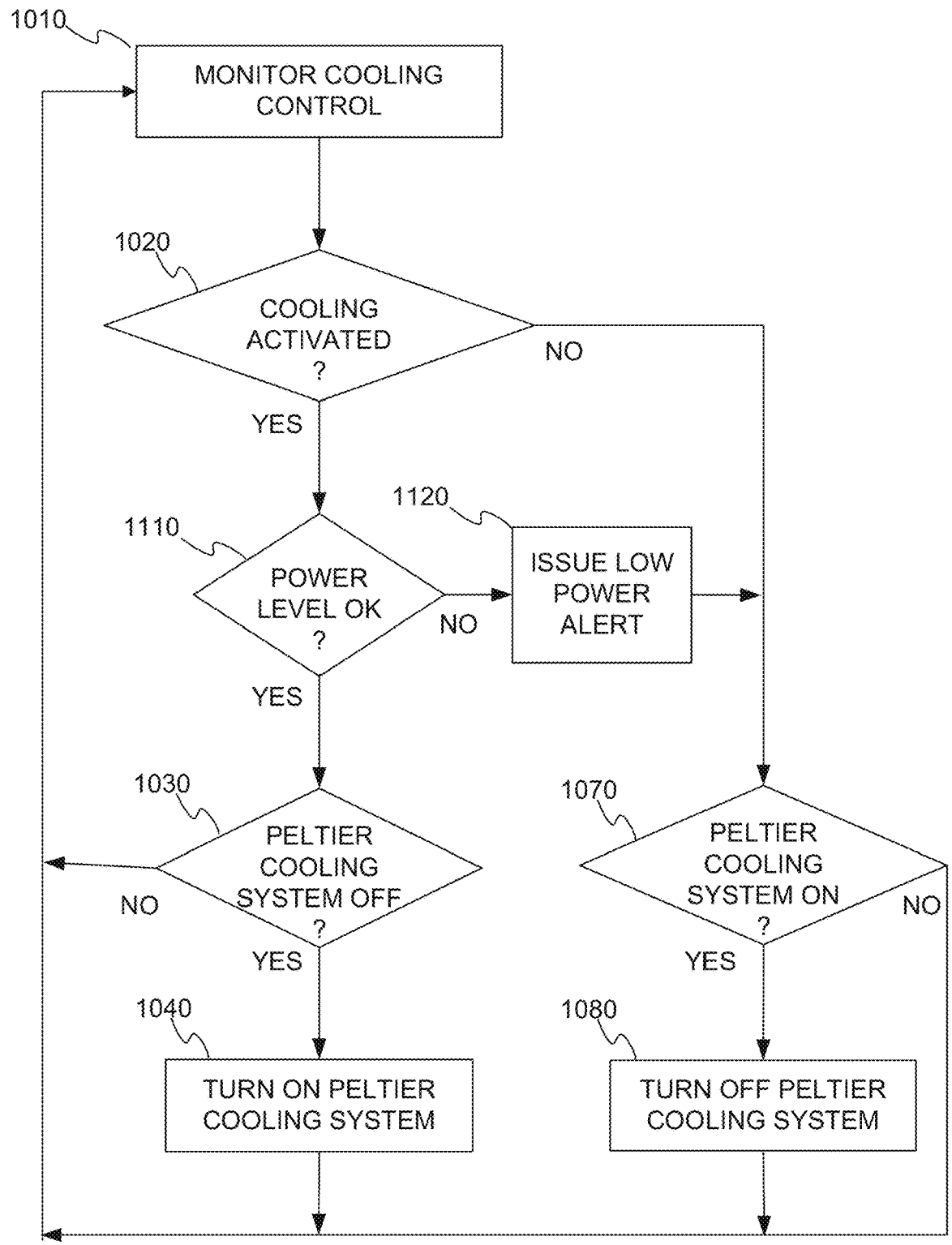
FIG. 11 is a flow diagram illustrating sample methods for use in a wearable medical device system to cool a portion of a patient and/or one or more patient sensors, according to embodiments.

FIG. 11 is a flow diagram illustrating embodiments of a method 1100 for use in wearable medical device systems (such as described above) to cool a portion of a patient and/or one or more patient sensors, according to embodiments. The process implemented by method 1100 may be performed by a temperature control module such as temperature control module 298 described above in conjunction with FIG. 2A in some embodiments. Method 1100 is similar to method 1000 (FIG. 10) with a low power alert functionality, thus the flow diagram is similar to FIG. 10 but with the insertion of blocks 1110 and 1120 after block "yes" decision of block 1020. The description of method 1100 begins with block 1110 below without repeating the description blocks of method 1000 (FIG. 10).

Block 1110 is performed when block 1020 determined or detected that the wearer activated the cooling system. In block 1110, the power level of the cooling system's power source is checked to see if remains above a predetermined level. If the power level is above this predetermined level, method 1100 proceeds to previously described block 1030. However, if the power level is not above the predetermined threshold, method 1110 proceeds to a block 1120. In some embodiments, the aforementioned temperature control module in block 1120 may also cause the cooling device to into a power generation mode (using the Seebeck Effect) such as previously described in conjunction with FIG. 7.

In block 1120, a low power alert or notification is issued. In some embodiments, the aforementioned temperature control module causes the user interface to provide an indication of the low power condition to the wearer. The indication can be audio, visual, haptic, vibration, etc. Method 1110 then proceeds to previously described block 1070.

Figure 12:
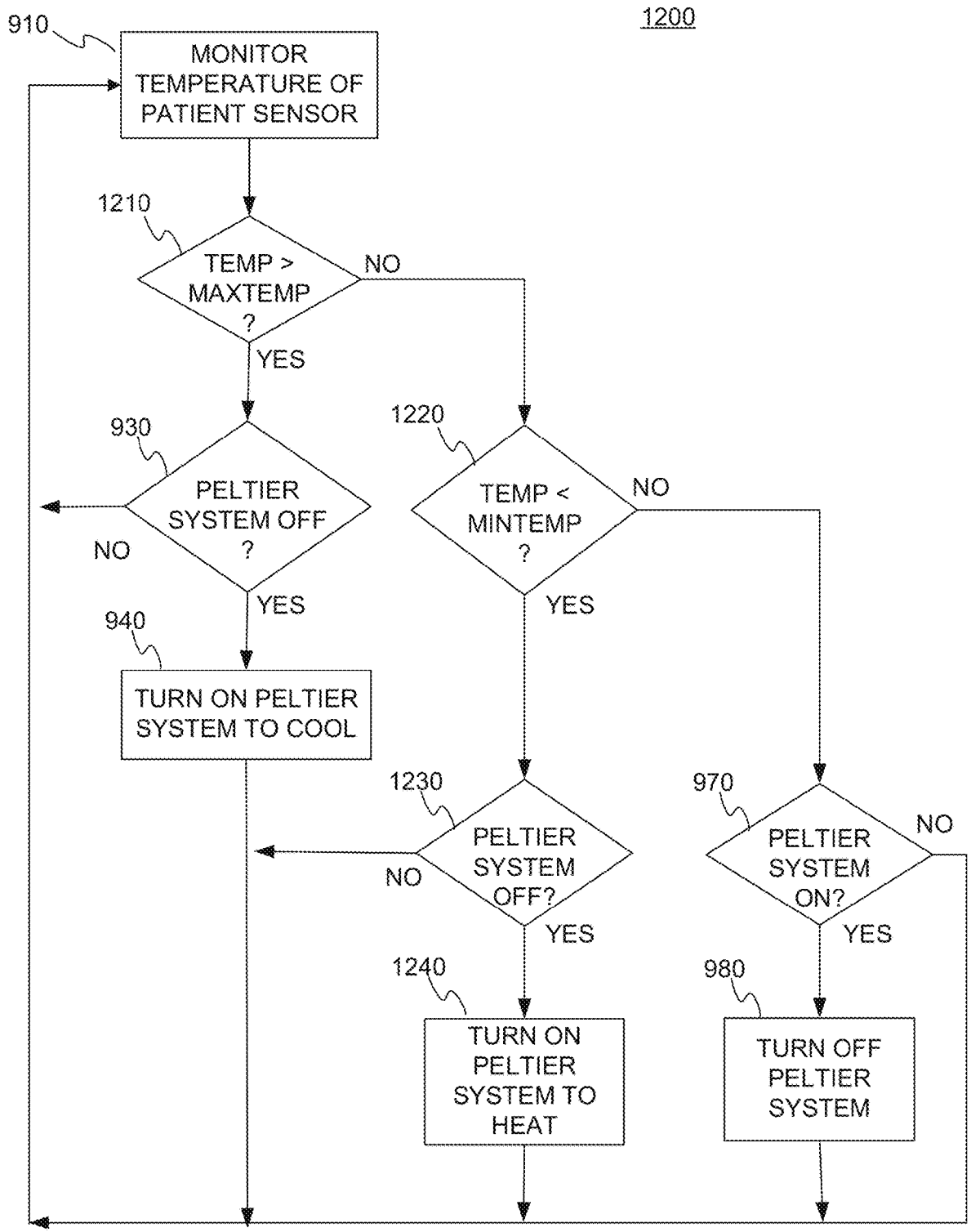
FIG. 12 is a flow diagram illustrating sample methods for use in a wearable medical device system to cool a portion of a patient and/or one or more patient sensors, according to embodiments.

FIG. 12 is a flow diagram illustrating embodiments of a method 1200 for use in wearable medical device systems (such as described above) to cool a portion of a patient and/or one or more patient sensors, according to embodiments. The process implemented by method 1200 may be performed by a temperature control module such as temperature control module 298 described above in conjunction with FIG. 2A in some embodiments. Method 1200 can be used to enable both heating and cooling based on a monitoring the temperature and comparing to a predetermined temperature range.

Method 1200 is similar to method 900 (FIG. 9), thus FIG. 12 is similar to FIG. 9. The description of method 1200 begins with block 1210 below without repeating the description blocks of method 900 (FIG. 9).

The temperature from block 910 is then analyzed in block 1210. If the temperature is above a max temperature, method 1200 proceeds to blocks 930 and 940 as previously described in conjunction with FIG. 9. However, if in block 910 the temperature is below the max temperature, method 1200 proceeds to a block 1220.

In block 1220, the temperature from block 910 is then analyzed. If the temperature is not below a min temperature, method 1200 proceeds to blocks 970 and 980 as previously described in conjunction with FIG. 9. However, if the temperature is below the min temperature, method 1200 proceeds to a block 1230.

In block 1230, the cooling system (e.g. a cooling device such as Peltier device 611A of FIG. 7) is checked to see if it is turned off. If the cooling device is turned off, method 1200 returns to block 910. However, if the cooling device is turned on, method 1200 proceeds to a block 1240 in which the cooling system is configured to a heating mode (e.g., by reversing the polarity of the voltage provided by the power source) and loops back to block 910.

In the methods described above, each operation can be performed as an affirmative step of doing, or causing to happen, what is written that can take place. Such doing or causing to happen can be by the entire system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention after careful review of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A wearable medical device (WMD) comprising:
   one or more monitor electrodes, the one or more monitor electrodes configured to receive electrocardiogram (ECG) signals from a patient;
   a plurality of therapy electrodes;
   a support structure configured to be worn by the patient, the support structure coupled to the one or more monitor electrodes and the plurality of therapy electrodes and configured to arrange the one or more monitor electrodes and the plurality of therapy electrodes proximate a skin of the patient;
   a monitoring device, the monitoring device being separate from the support structure, being communicatively coupled with the one or more monitor electrodes and the plurality of therapy electrodes, having an energy storage device and an output circuit, and having circuitry communicatively coupled with the one or more electrodes and the plurality of therapy electrodes, wherein the monitoring device is configured to provide electrical shock therapy to the patient using the energy storage device, the output circuit and the plurality of therapy electrodes;
   a Peltier device thermally coupled with at least one of the one or more monitor electrodes and/or one of the plurality of therapy electrodes, the Peltier device configured to cool a portion of the at least one of the one or more monitor electrodes and/or one of the plurality of therapy electrodes; and
   a temperature control module configured to cause the Peltier device to cool the portion when the WMD is not providing therapy via the plurality of therapy electrodes and stopped when the WMD is preparing to deliver therapy.

2. The WMD of claim 1 further comprising one or more sensors coupled to the support structure, wherein the one or more sensors are communicatively coupled with the monitor device and configured to monitor a temperature of the portion of the skin of the patient.

3. The WMD of claim 1, wherein the energy storage device comprises a capacitor, and the output circuit comprises an H-bridge.

4. The WMD of claim 1, wherein the monitor device further comprises a power source.

5. The WMD of claim 4, wherein the Peltier device is electrically coupled to the power source and has a first operating mode and a second operating mode, wherein:
   in the first operating mode the Peltier device is configured to cool the portion of the at least one of the one or more monitor electrodes and/or one of the plurality of therapy electrodes, and
   in the second operating mode the Peltier device is configured to charge the power source.

6. The WMD of claim 5, wherein the Peltier device comprises the Peltier device configured to enter the first operating mode responsive to receiving an input from the patient.

7. The WMD of claim 1, wherein the Peltier device is in contact with a thermally conductive portion of the support structure that is proximate to the portion of the at least one of the one or more monitor electrodes and/or one of the plurality of therapy electrodes.

8. The WMD of claim 1 further comprising defibrillation circuitry electrically coupled with the energy storage device and with the output circuitry, wherein the defibrillation circuitry is configured to selectively receive power from the energy storage device and deliver an electric shock to the patient.

9. The WMD of claim 1, wherein the Peltier device is integrated with the support structure.

10. A wearable cardioverter defibrillator (WCD), comprising:
  one or more monitor electrodes, the one or more monitor electrodes configured to receive electrocardiogram (ECG) signals from a patient;
  a plurality of therapy electrodes;
  a support structure configured to be worn by the patient, the support structure coupled to the one or more monitor electrodes and the plurality of therapy electrodes and configured to arrange the one or more monitor electrodes and the plurality of therapy electrodes proximate a skin of the patient;
  an external defibrillator, the external defibrillator being separate from the support structure, the one or more monitor electrodes and the plurality of therapy electrodes, being communicatively coupled with the one or more monitor electrodes and the plurality of therapy electrodes, having an energy storage device and an output circuit, and having circuitry communicatively coupled with the one or more electrodes and the plurality of therapy electrodes, wherein the external defibrillator is configured to provide electrical shock therapy to the patient using the energy storage device, the output circuit, and the plurality of therapy electrodes;
  a Peltier device separate from the external defibrillator, the Peltier device being configured to cool a portion of the patient's skin; and
  a temperature control module configured to cause the Peltier device to cool the portion when the WCD is not providing electrical shock therapy by directing airflow through channels of the plurality of therapy electrodes used for dispensing gel onto the patient's skin.

11. The WCD of claim 10 further comprising one or more sensors coupled to the support structure, wherein the one or more sensors are communicatively coupled with the monitor device and configured to monitor a temperature of the portion of the skin of the patient.

12. The WCD of claim 10, wherein the airflow is directed to the channels by tubing thermally coupled to the Peltier device.

13. The WCD of claim 10, wherein the external defibrillator device further comprises a power source.

14. The WCD of claim 13, wherein the Peltier device is electrically coupled to the power source and has a first operating mode and a second operating mode, wherein:
  in the first operating mode the Peltier device is configured to cool the portion of the at least one of the one or more monitor electrodes and/or one of the plurality of therapy electrodes, and
  in the second operating mode the Peltier device is configured to charge the power source.

15. The WCD of claim 14, wherein the Peltier device comprises the Peltier device configured to enter the first operating mode responsive to receiving an input from the patient.

16. The WCD of claim 10, wherein the Peltier device is in contact with a thermally conductive portion of the support structure that is proximate to the portion of the at least one of the one or more monitor electrodes and/or one of the plurality of therapy electrodes.

17. The WCD of claim 10, wherein the Peltier device is integrated with the support structure.

18. A method for configuring a wearable medical device (WMD) that is worn by a patient, the method comprising:
  coupling one or more monitor electrodes to a support structure, the one or more monitor electrodes configured to receive electrocardiogram (ECG) signals from a patient;
  coupling a plurality of therapy electrodes to the support structure;
  coupling one or more sensors to the support structure, wherein the one or more sensors are configured to monitor a temperature of a portion of a skin of the patient;
  coupling an energy storage device to the support structure;
  electrically coupling an energy storage device to a Peltier device, wherein the Peltier device has a first operating mode that cools the portion of the skin of the patient and a second operating mode that charges the energy storage device;
  communicatively coupling the one or more monitor electrodes, the plurality of therapy electrodes, the one or more sensors, the energy storage device, and the Peltier device to a processor; and
  programming the processor to execute a procedure, wherein the procedure when executed causes the processor to:
    receive the temperature of the portion of the skin of the patient from the one or more sensors,
    cause the Peltier device to enter the first operating mode when the temperature exceeds a first threshold to cool the portion of the skin of the patient when the WMD is not providing therapy to the patient via the plurality of therapy electrodes, and
    cause the Peltier device to enter the second operating mode when the temperature is less than a second threshold.

19. The method of claim 18, wherein the procedure further causes the processor to:
  receive an input from the patient, and
  cause the Peltier device to enter the first operating mode in response to receiving the input from the patient.

20. The method of claim 18, wherein the Peltier device is in contact with a thermally conductive portion of the support structure that is proximate to at least one of the one or more monitor electrodes and/or one of the plurality of therapy electrodes to cool the portion of the skin of the patient.

21. The method of claim 18, wherein the procedure further causes the processor to:
  stop cooling when the WMD is preparing to deliver therapy; and
  cause a charge from the energy storage device to be delivered to the patient based via the plurality of therapy electrodes, at least in part, on an analysis of one or more output signals from at least one of the one or more monitor electrodes.

* * * * *